(12) United States Patent
Noras (10) Patent No.: US 8,620,407 B2
(45) Date of Patent: Dec. 31, 2013

(54) PATIENT SUPPORT

(76) Inventor: Hubert Noras, Wurzburg (DE)

( * ) Notice: Subject to any disclaimer, the term of this patent is extended or adjusted under 35 U.S.C. 154(b) by 1496 days.

(21) Appl. No.: 11/886,736

(22) PCT Filed: Mar. 16, 2006

(86) PCT No.: PCT/DE2006/000456
§ 371 (c)(1),
(2), (4) Date: Sep. 20, 2007

(87) PCT Pub. No.: WO2006/099841
PCT Pub. Date: Sep. 28, 2006

(65) Prior Publication Data
US 2009/0054757 A1    Feb. 26, 2009

(30) Foreign Application Priority Data

Mar. 22, 2005   (DE) .......................... 10 2005 013 151

(51) Int. Cl.
*A61B 5/05*     (2006.01)

(52) U.S. Cl.
USPC ................................ 600/422; 5/613; 600/415

(58) Field of Classification Search
None
See application file for complete search history.

(56) References Cited

U.S. PATENT DOCUMENTS

| 5,297,303 A | 3/1994 | Stafford et al. |
| 5,569,266 A | 10/1996 | Siczek |
| 5,865,181 A | 2/1999 | Spence, Jr. |
| 6,446,286 B1 | 9/2002 | Karmalawy |
| 2001/0039378 A1 | 11/2001 | Lampman et al. |
| 2004/0068180 A1* | 4/2004 | Collins et al. ................. 600/425 |
| 2005/0080333 A1* | 4/2005 | Piron et al. .................... 600/417 |

FOREIGN PATENT DOCUMENTS

DE      196 26 286 A1    1/1998

* cited by examiner

*Primary Examiner* — Long V. Le
*Assistant Examiner* — Nicholas Evoy
(74) *Attorney, Agent, or Firm* — Mattingly & Malur, PC (57) ABSTRACT

A patient support includes an upper support plate which is provided with a headrest. A base plate is arranged below, and separate from the upper support plate, by a floating mounting. A single narrow, narrow support column is provided, in the region of the headrest, between the support plate and the base plate. An upper face of the support plate consists of a forward zone, a mid-zone and an end zone. A width of the support plate reduces continuously from a widest point in the forward zone to a narrow space in the mid-zone and then widens continuously to the end of the support plate. Left and right sections of the patent support are formed and run horizontally arranged symmetrically about a longitudinal and symmetrical axis of the support plate.

30 Claims, 5 Drawing Sheets

PATIENT SUPPORT

CROSS-REFERENCE TO RELATED APPLICATIONS

This application is the U.S. national phase, under 35 USC 371, of PCT/DE2006/000456, filed Mar. 16, 2006; published as WO 2006/099841 A1 on Sep. 28, 2006 and claiming priority to DE 10 2005 013 151.4, filed Mar. 22, 2005, the disclosures of which are expressly incorporated herein by reference.

FIELD OF THE INVENTION

The subject invention is directed to a patient support. The patient support includes an upper support plate and a base plate which is spaced from, and beneath the upper support plate.

BACKGROUND OF THE INVENTION

Patient supports, which may be equipped with a breast immobilizing device, a biopsy device or a marking device, are generally known in the art. Such patient supports have two openings in an upper support plate, into which openings the patient's breasts can be placed, freely hanging, for examination. The upper support plate is supported against a lower base plate, which is spaced several centimeters from it, typically via multiple, such as, for example, four support pillars.

DE 196 26 286 C2 shows an MRI breast coil with a device for immobilizing a breast for biopsy. This device comprises a patient support with an upper support plate having two openings and also having breast pressing elements, spaced from one another. A breast is placed in a space between these pressing elements, and the breast is ultimately immobilized by bringing the pressing elements together, after which immobilization, the breast can be biopsied, for example.

SUMMARY OF THE INVENTION

The object of the present invention is to provide a patient support configured with an upper support plate and with a base plate spaced horizontally from the upper support plate, in which space, an access area to provide the accessibility to the breast(s), which are suspended in the space between the support plate and the base plate, is significantly expanded for diagnostic and/or interventional measures, and in which space, breast immobilizing apparatus can be used.

This object is attained by the provision of a patient support having an upper support plate and a base plate which is arranged beneath, and spaced from the support plate. The support plate has a cantilevered portion with a head support surface. A single, weight-bearing, narrow support pillar supports the upper support plate and spaces it from the base plate.

The advantages of the present invention consist especially in that the patient support of the present invention can accommodate a device for immobilizing a breast, with or without a device for biopsying or marking a defect in the tissue structure inside the breast. A very large slewing angle range around a vertical or perpendicular pivoting axis is provided for the aforementioned device. In a forward portion of an intermediate space between the support plate on the top and the base plate on the bottom, as viewed in the direction of the support plate's longitudinal axis, up to the area of an opening or a recess for the breast, up to the start or the headrest area of the head support surface of the support plate, one or more narrow and short support elements is/are provided. These or this support elements or element are crossing through the intermediate space in a horizontal and a vertical direction, and serve to support the support plate. The upper support plate can still be advantageously extended far enough lengthwise that the head, or at least the upper body of the patient resting on the patient support, can be supported, or can rest directly or indirectly on the upper support plate. In this manner, the need for additional headrests outside of, or in front of the patient support, which would impede access to the immobilized breast in the direction of the head/feet, is advantageously eliminated. A further advantage of the present invention is that the patient support can be used, for example, in computer tomography (CT), magnetic resonance imaging (MRI) or positron emission tomography (PET). The patient support, in accordance with the present invention permits, in an inventive manner, the arrangement of one or more receiving surface coils without significantly decreasing the rotational range of an immobilization and/or a biopsy device to be used. The receiving surface coils can be mounted, oriented horizontally, in or on the base plate. Horizontally oriented receiving surface coils can also be mounted directly or indirectly on the support plate, and can also be horizontally and/or vertically displaceable, for example.

A device for immobilizing a breast, with or without a holder for a medical tool, such as a biopsy or a marking tool can be easily inserted into and removed from the patient support.

BRIEF DESCRIPTION OF THE DRAWINGS

A preferred embodiment of the present invention is represented in the set of drawings and will be described in greater detail in what follows.

The drawings show in.

DESCRIPTION OF THE PREFERRED EMBODIMENTS

Computer tomography (CT) is a diagnostic procedure in which the region of a human body to be examined is irradiated by a focused x-ray bundle via an x-ray tube rotating around the body.

In magnetic resonance imaging (MRI), images of the human body are generated without the use of ionizing radiation, or in other words, without the use of x-rays or radioactive materials.

Positron emission tomography (PET) is a highly sensitive procedure with which metabolic processes in the body can be visualized.

With CT, MRI, and PET examination, the location of an anomaly in an immobilized breast can be precisely measured within an orthogonal system of coordinates. These location defining values can be manually or automatically preset in a medical tool, such as a biopsy needle, outside or inside the MRI coil, on a tool holder that can be adjusted horizontally and vertically using dials. The preset medical tool holder can be easily inserted into the patient support.

Figure 1:
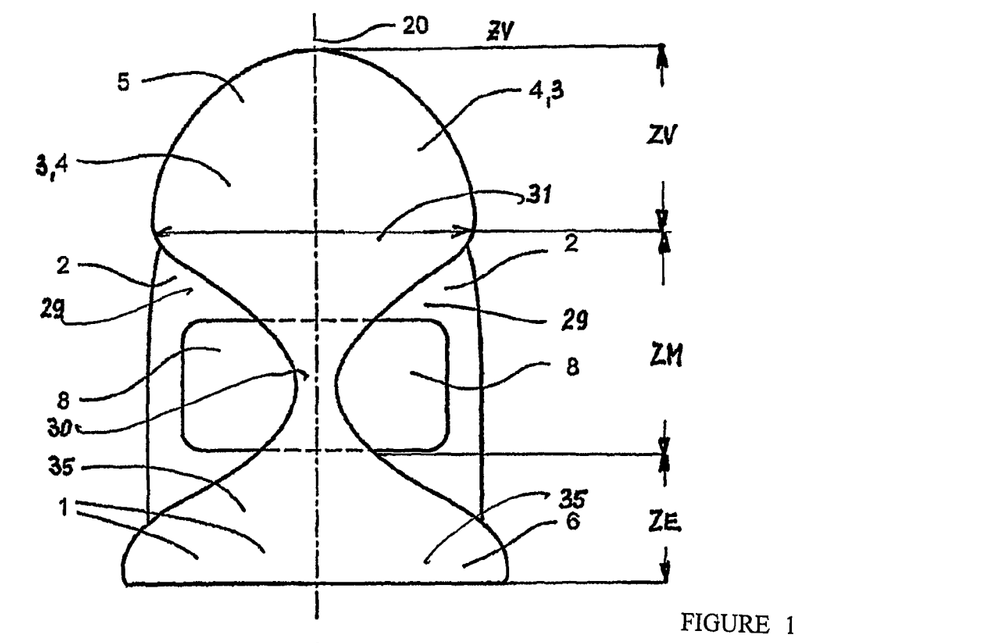
FIG. 1, a top plan view of the patient support in accordance with the present invention, with a view of a, for example, rectangular mounting recess in the base plate for a mounting plate for a device for immobilizing a breast, with or without a holder for a medical tool, such as a biopsy or a marking tool for a breast and/or for one or more horizontally oriented MRI receiving surface coils FIG. 2, a top plan view in accordance with FIG. 1, and with a mounting plate installed in the mounting recess FIG. 3, a front perspective view of the patient support of FIG. 1, with a view of the front support surface in accordance with the present invention with a cantilevered head section with a head support surface, which transitions in the direction of the patient's feet into a narrow bridge, and ultimately is attached, at the end of the support plate, via its upper body support section, to the end plate, which extends in a vertical and a horizontal direction FIG. 4, a perspective end view of an end plate of the patient support, which connects the ends of the support plate and the base plate and extends in a vertical direction FIG. 5, a plan view of the upper side of the mounting plate with two conical mounting holes, each equipped with internal teeth.
Figure 2:
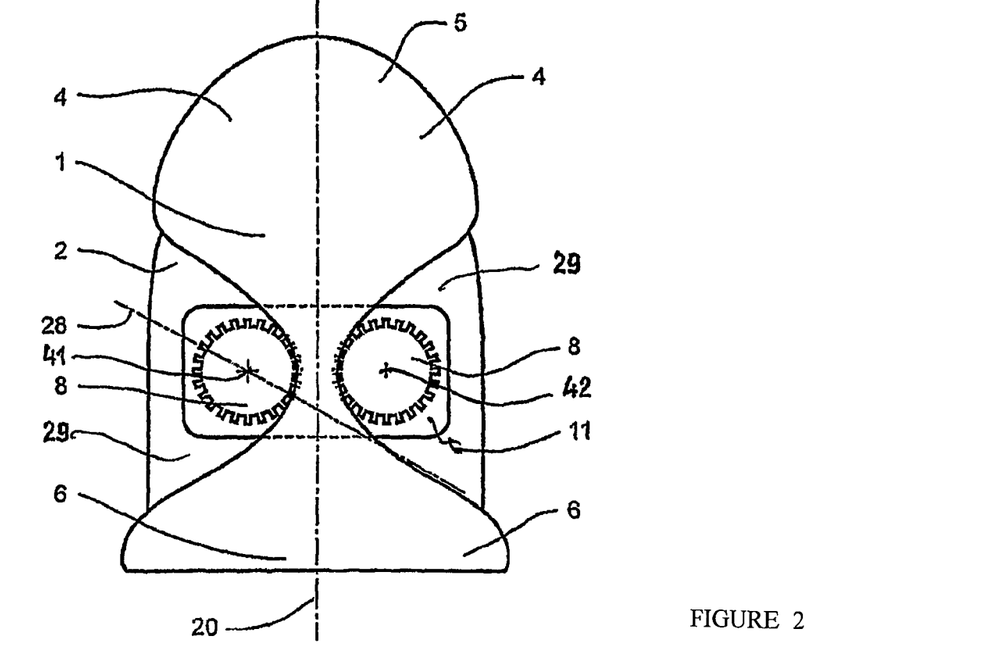
Figure 3:
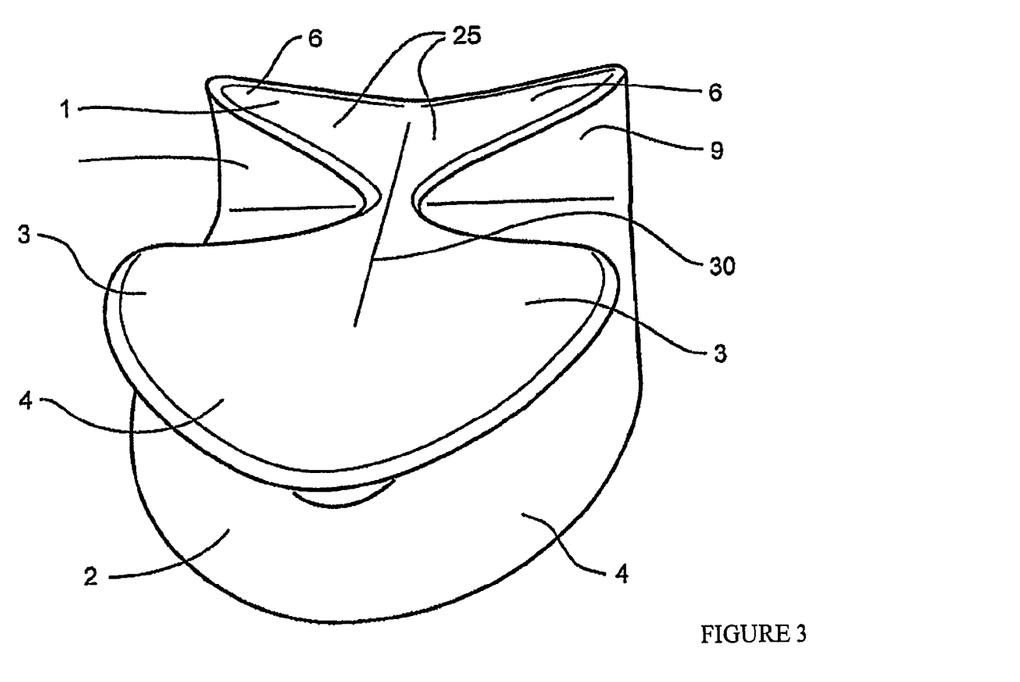
Figure 4:
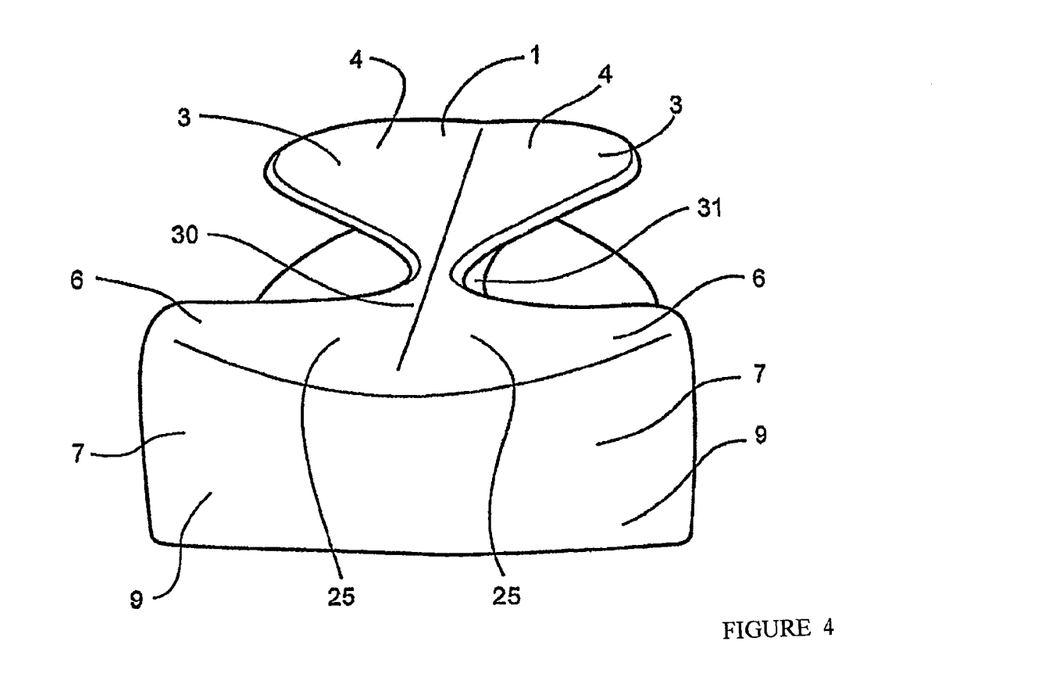

Referring initially to FIG. 1, patient support 1, in accordance with the present invention, is comprised of a base plate 2 that extends in a horizontal direction, and a support plate 3, which is arranged above the base plate 2 at a spacing h and extending in a horizontal direction. Between these two plates 2 and 3, an intermediate space 14 is provided. The spacing h, such as, for example, of 80-100 mm between an underside 27 of support plate 3 and an upper side 29 of the base plate 2 need not be equal over the entire length of the patient support 1. A longitudinal axis of symmetry 20 divides the outer surface of the support plate 3 into a left surface part and a right surface part. All the components of the patient support 1 are made of an MR-appropriate material, such as, for example, plastic or the like.

Figure 7:
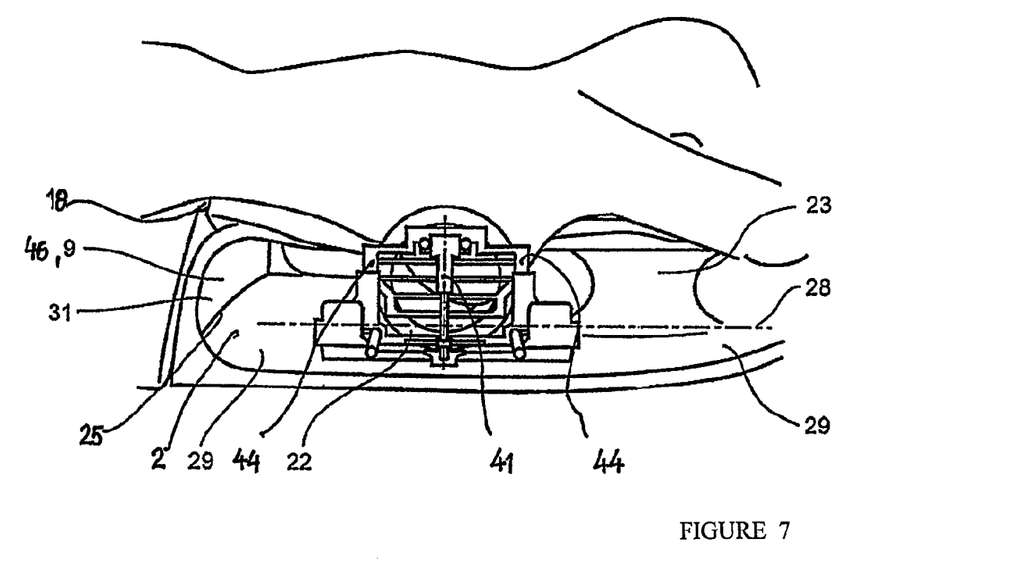
Figure 8:
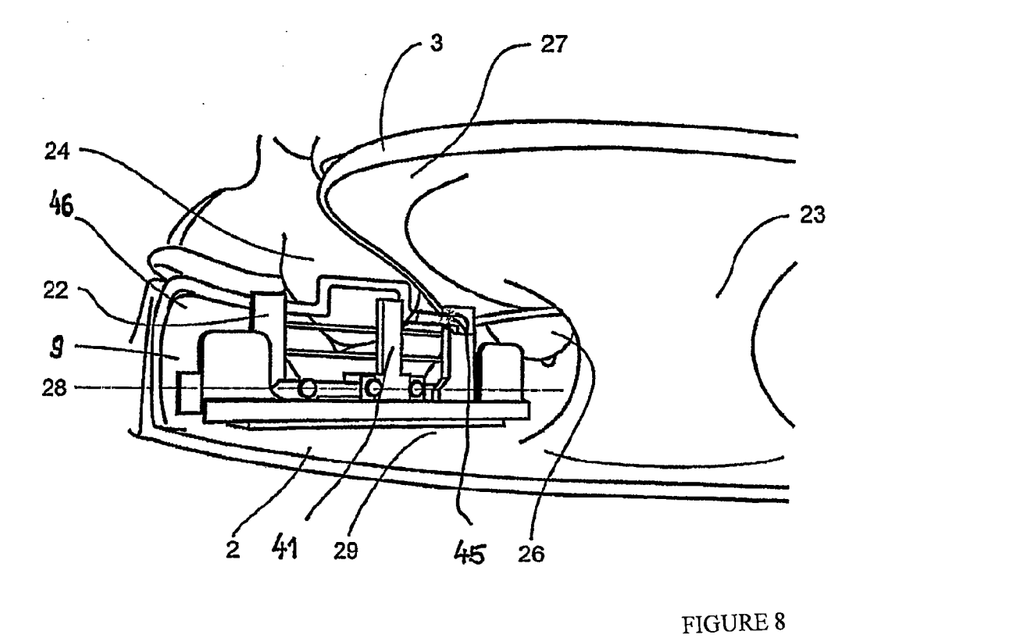
Figure 9:
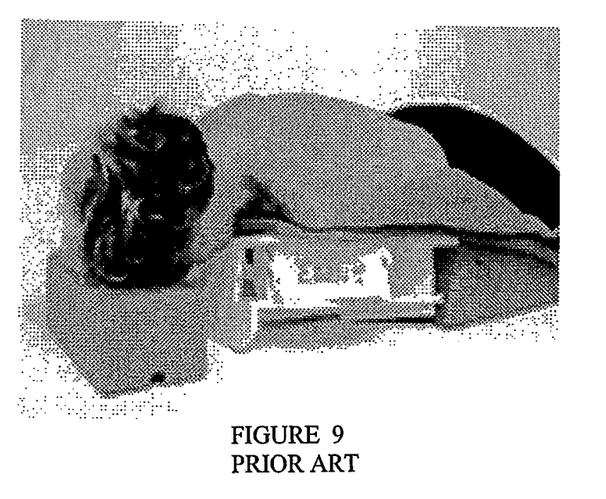

The support plate 3 is comprised essentially of three main zones along its longitudinal axis 20, starting at the head end A front zone ZF with a head support surface 4 of a head section 5. This front zone extends, for example, over approx. 35% of the length of the support plate 3. The front zone ZF serves as the support surface for the head and the shoulder area of a patient, as seen in FIG. 7. Under the front zone ZF of the upper support plate 3, or in other words in the front part of the intermediate space 14, one or more narrow support elements or support pillars 23, which are short relative to the overall length of the patient support, is/are preferably provided along or spaced laterally from a vertical plane that spans the longitudinal and symmetrical axis 20 in a perpendicular orientation. The support element or elements 23 is or are adhesively or positively connected to the underside of the upper support plate 3 and to the upper side of the base plate 2. In the preferred embodiment, the upper and/or lower part of the support element, or elements 23 is or are configured as pressure distribution plates, which are adhesively or positively connected to the underside of the support plate 3 and/or to the upper side of the base plate 2. For this reason, the upper and lower ends of each of the support element or elements 23 is or are widened into a mushroom shape.

The support element or elements 23 is or are arranged at a slight distance, such as, for example, at 70 to 150 mm, from the forward edge of the head support plate 3. If only a single support element 23 is used, it is, for example, 10 to 150 mm wide and is, for example, 10 to 200 mm long at its narrowest point.

The position of the support element, or elements 23 and the height h of the intermediate space 14 are configured such that a device for immobilizing a breast, with or without a holder for a medical tool, such as a biopsy or a marking tool 22, hereinafter abbreviated to device 22 can be rotated approximately 360° in each of its working positions, preferably around a perpendicular axis at the respective instantaneous center of rotation of the horizontally aligned receiving surface coil. The rotational motion of the device 22 therefore is not impeded by obstructions.

Figure 10:
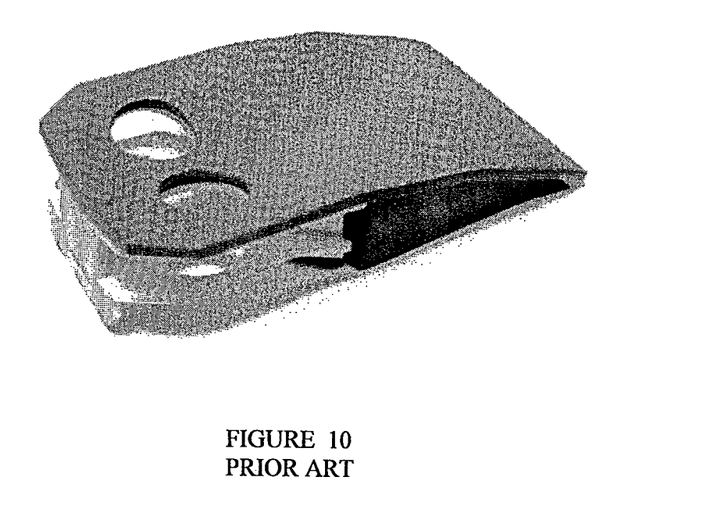

With the advantageous positioning of the support element or elements 23, the upper support plate 3 of the patient support 1 can advantageously be extended in a patient cranial direction far enough so that the head of the patient, who is lying with at least her upper body on the support plate 3, again as seen in FIG. 7, can be supported or rested directly or indirectly on the patient support 1. This advantageously eliminates the need for a patient support which would be arranged outside of, such as, for example, in front of the patient support. Such a support would make access to an immobilized left breast 24 or right breast 26, viewed in the head-foot direction, impossible in the caudal or head-foot direction. In this regard note the prior art which is represented in FIGS. 10 and 11.

A center zone ZC, also referred to as the "chest zone," is adjacent to the front zone ZF of the patient support 1 in the caudal direction of the support plate 3. This center zone ZC extends, for example, over approx. 50% of the length of the support plate 3. It has the form of, for example, a bridge 30 that narrows for half of its length and then widens again. This center zone surface supports the patient's sternum. To the left and to the right of the longitudinal and symmetrical axis 20 of the bridge 30, the bridge 30 widens to define a left cut-out 33 and, opposite that, to the right of the longitudinal and symmetrical axis 20, a right cut-out 32. The left cut-out 33 is open to the outside on the left of the bridge 30, the right cut-out 32 is open to the outside on the right of the bridge 30, as seen in FIG. 1. The bridge 30 can be between 40 mm and 100 mm wide, for example, at its narrowest point. The contours of the cut-outs 32 and 33 can each take the shape of a horizontal parabola, in a horizontal plane or in a plane that is inclined upward or downward in relation to that horizontal plane. Their vertices can be spaced at equal or unequal distances from the longitudinal and symmetrical axis 20, although equal spacing is preferable. These cut-outs 32 and 33, which open wide toward the outside of the support plate 3, enable even larger breasts to hang through the respective cut-outs freely and very deeply, before being immobilized. Furthermore, they permit an expanded, unobstructed view of the device 22 with the immobilized breast 24 and/or 26.

This is particularly important because the device for immobilizing a breast with the device 22 can be rotated or turned around its vertical axis up to 360°, continuously or in small steps, before the breast is immobilized, and can then be detachably secured against torsion.

The end zone ZE or the end surface of the support plate 3 extends to the rear of the bridge 30. Beginning at the end of the support plate bridge 30, it extends over approx. 15% of the length of the support plate 3. It serves as the support surface 6 for the upper part of the user's abdomen, adjacent to the chest—as viewed in the direction of the feet. In this regard, see FIGS. 1 and 7.

The support surface 6 of the end zone ZE of the support plate 3 ends at the end plate 9, which end plate 9 extends both vertically and horizontally. The end of the support plate 3 is preferably adhesively or positively connected to an upper part 7 of the end plate 9. A lower part 10 of the end plate 9 is adhesively or positively connected to the end of the base plate 2.

With the elevated projection of the left cut-out 33 and of the right cut-out 32 in the intermediate space 14, an imaginary left planar section 39 and an imaginary right planar section 40, respectively, are formed on the upper side 29 of the base plate 2. The device for immobilizing a breast 22, with or without a holder for a medical tool or a biopsy, or marking tool is arranged in the left 49 and/or the right working space 50 bounded in this fashion.

Therefore, the area below the cut-outs 32, 33 and consisting of the left 49 andor the right working space 50 and the bridge 30 is the area in which the device 22 is arranged. As described above, device 22 can be rotated 360° around a vertical axis.

The slewing or rotational motion of the device 22 is advantageously not impeded or restricted by obstructions.

Figure 5:
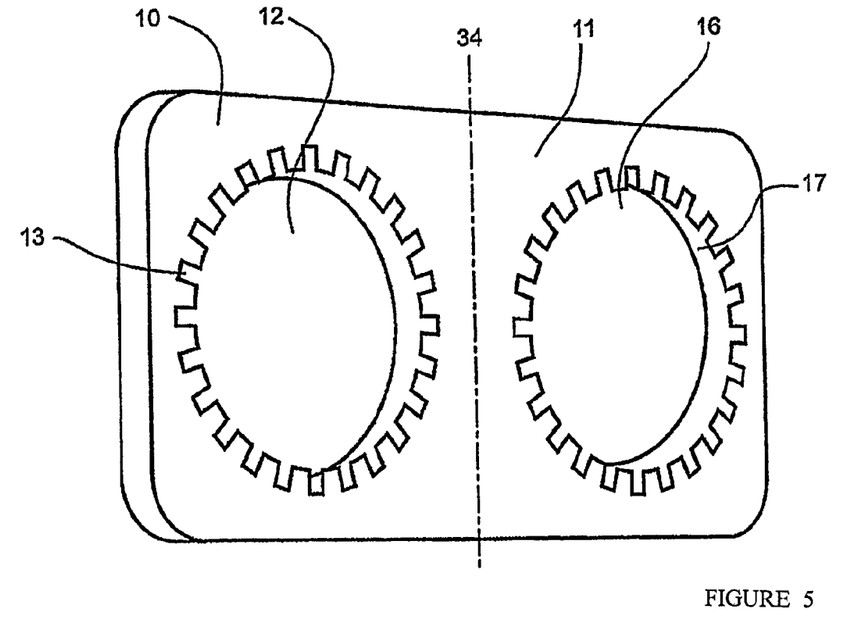

A rectangular mounting plate 11, as seen in FIG. 5, the length of which corresponds nearly to the entire width of the base plate 2 in the area of the bridge 30 of the support plate 3, is removable, and is mounted, in a positive manner, in a mounting recess 8 or in a mounting hole 8, such as by, for example, a guide, such as a flat or dovetailed guide. The mounting recess 8 or mounting hole 8 is integrated into the base plate 2, and is open to its upper side. The mounting plate 11 has, for example, two circular, continuous mounting holes 12; 16, which are preferably equal in diameter. The centers of the two mounting holes 12; 16 and therefore the centers of the receiving surface coils 37, 38 have unequal spacings a and b, with a difference, for example, of 3 to 4 cm, from the transverse center line 34 of the mounting plate 11. The reason for this difference in the spacings a and b is the advantageous capability of adjusting to different upper body widths and/or breast spacing in the patients being examined.

Figure 6:
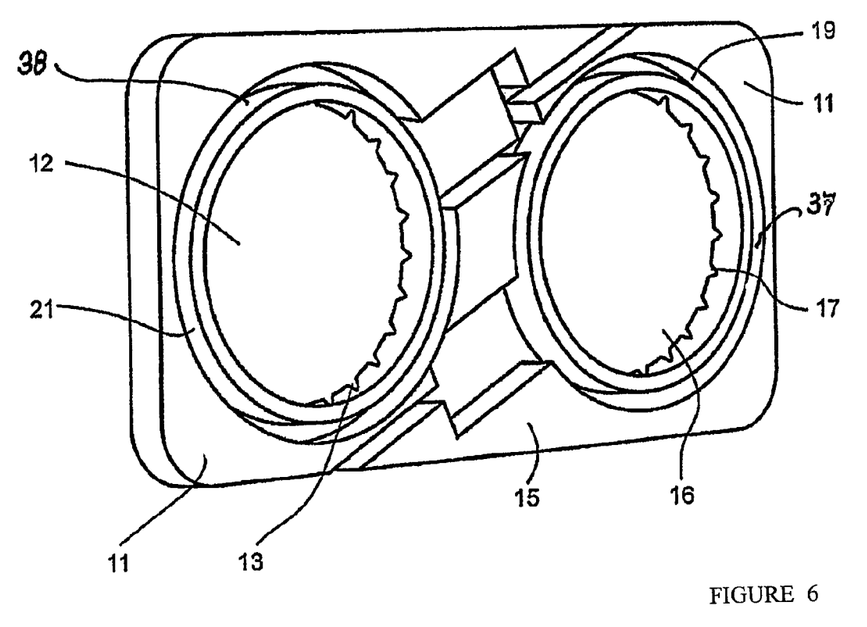
in FIG. 6, a view of the underside of the mounting plate according to FIG. 5, with one annular groove incorporated into each mounting hole, concentrically thereto, in the underside of the mounting plate, and configured to accommodate a receiving surface coil FIG. 7, a right side view of the patient support of the present invention, with a patient lying with the front side of her upper body resting on the support plate and also with a device for immobilizing a breast, which is oriented, non-rotatably, parallel to the longitudinal axis of the support plate, with two immobilization grids that can be moved toward one another in an adjustable spacing, and with a device for biopsying or marking a defect in the tissue structure inside the breast FIG. 8, a view, between the underside of the head section of the head support plate and the upper surface of the base plate, of a device for immobilizing a breast with a device for biopsying or marking the breast, a vertical plane of that immobilizing device, that extends along its longitudinal axis, intersecting a vertical plane that extends along the longitudinal and symmetrical axis of the support plate in an adjustable angle of intersection FIGS. 9 and 10 patient supports in accordance with the prior art.

The mounting holes 12; 16 in the mounting plate 11 are each equipped, for example, with internal toothing 13; 17. The underside 15 of the mounting plate 11, which is shown in FIG. 6 is provided with an annular left groove 21, which is configured to accommodate a left receiving surface coil 38, and an annular right groove 19, which is configured to accommodate a right receiving surface coil 37, each groove 19, 21 being integrated concentrically in relation to its respective mounting hole 12; 17 in the underside 15 of the mounting plate 11.

So that the device 22, without the immobilized breast can be rotated or can be turned up to 360° on its vertical axis, either continuously or in small steps, and can then be detachably secured against torsion, a collar, for example in the form of a circular ring, for example with an exterior cone, is applied, for example, to the underside of the base plate 2 of the device 22, in an adhesive or positive connection. The circular ring is equipped, for example, with a ring gear having a conical exterior. The collar can be placed in positive connection with a receptacle configured to fit it. The collar and the receptacle thus form a coupling. This coupling can be configured, for example, as a switchable and optionally as a detachable positive coupling or as a non-positive coupling. In the preferred embodiment, a switchable, positive coupling, such as a toothed coupling, is used.

The teeth of the externally conical toothed ring or collar can be respectively placed in and taken out of engagement, i.e. coupled and decoupled, with the internal toothing 13; 17 of the, for example, two conical mounting holes 12; 16 or mounts of a mounting plate 11 for the device 22. They thus form a switchable, and preferably on optionally detachable, positive coupling.

To couple and decouple, and to rotate the device 22 around its vertical axis, the device is first raised, thereby detaching its conical external toothing from the allocated internal toothing 13; 17 of the first mounting hole 12 and/or the second mounting hole 16, after which the device 22 is turned or rotated a selectable angle around its vertical axis, and is then placed back in engagement. As described above, the applicable coupling mode is not limited to the toothed coupling principle. Other positive coupling methods, and non-positive couplings, such as cone friction couplings, could also be used.

The mounting plate 11 with the two mounting holes 12, 16 can also be shorter in structure, so that it can be displaced crosswise to the longitudinal axis 20, guided by a suitable guide, and then can be locked in place in a desired position via a locking device that operates in a non-positive or in a positive fashion. To save on overall height, the mounting plate 11 can be displaced in the mounting recess 8 or the mounting hole 8.

The mounting plate 11 can also be provided with only with one mounting hole 12 for only one MRI receiving surface coil 38. In that case, only one MRI receiving surface coil 38 would be necessary, which would be used to examine both the left breast and the right breast. The accordingly short mounting plate would then need only to be shifted from the left side to the right side, crosswise to the direction of the longitudinal axis 20, via a guide.

In addition to the lower left receiving surface coil 38, which extends horizontally, and/or the lower right receiving surface coil 37, which extends horizontally, in the base plate 2 and/or in the mounting plate 11, an additional upper left 47 or upper right receiving surface coil 48 that extends horizontally can be provided, in order to improve image quality. These coils, which are also referred to as upper receiving surface coils, are attached directly or indirectly to the support plate 3, such as, for example, to a cushion on the patient support 1. The upper left and lower left receiving surface coils form a breast coil pair oriented horizontally on the left. The upper right and the lower right receiving surface coils form a breast coil pair that is oriented horizontally on the right. The centers of the left and right breast coil pairs should lie at a common left perpendicular and at a common right perpendicular, respectively. The upper receiving surface coils are made of metal and are insulated against electrical current and heat. They have the shape, for example, of a circular ring that is separated at some point through its entire ring width, giving the circular ring two connecting ends. The upper receiving surface coils are rigid in structure. They are preferably fastened to the bridge 30 at the area of their connecting ends, and are electrically connected. The upper receiving surface coils project outward from the bridge 30 to the left or right into the left cut-out 32 or into the right cut-out 33, respectively, oriented horizontally.

The device for immobilizing a breast, with or without a holder for a medical tool, such as a biopsy device or a marking tool 22 can have two vertically oriented receiving surface coils, specifically a left and a right receiving surface coil, spaced from one another. The vertical receiving surface coils are preferably attached to the two immobilizing grids.

In this case, the upper horizontal receiving surface coil, the right vertical receiving surface coil, the lower horizontal receiving surface coil, and the left vertical receiving surface coil together form a coil array.

In what now follows, the subject of the application will be summarized again:

The patient support 1 in accordance with the present invention is comprised of an upper support plate 3 and a base plate 2, which base plate 2 is arranged beneath and is spaced somewhat from the upper support plate 3. The two are separated from one another by an intermediate space 14. The upper support plate 3 has, in its front zone ZF, a cantilevered part with a head support surface 4. In the area of the head support surface 4 of the support plate 3, between its underside 27 and an upper side 29 of the base plate 2, the load bearing, narrow support pillar 23 is provided. It is connected in a positive or adhesive fashion to the upper side 29 of the base plate 2 and to the underside 27 of the support plate 3.

Viewed crosswise to the longitudinal axis 20 of the support plate 3, the support pillar 23 is narrow, for example, is 1 cm to 15 cm wide, as compared with the width of the support plate 3 and viewed in the direction of the longitudinal axis 20, is short in relation to the length of the support plate 3, such as, for example, is 1 cm to 20 cm long.

The end 25 of the base plate 2 is adhesively or is positively connected to the end 18 of the support plate 3 by the provision of an end plate 9 that extends vertically and horizontally.

The directions of the longitudinal axes of the support pillars 23 of the support plate 3 can extend in any opening angle in relation to one another, however, such an angle is preferably equal to zero degrees or to a few degrees, for example up to plus/minus 10°.

It is especially beneficial when the vertical plane along the longitudinal axis of the support pillar 23 and the vertical plane along the longitudinal axis 20 of the support plate 3 coincide.

The vertical plane along the longitudinal axis of the support pillar 23 and the vertical plane along the longitudinal axis 20 of the support plate 3 can, however, also be spaced horizontally from one another.

The upper support plate surface width 31 of the support plate surface 6 of the support plate 3 has at least three successive surface zones, starting at its forward edge and continuing to its trailing end 18: a front zone ZF, a center zone ZC that follows the first front zone ZF, and an end zone ZE that follows the center zone ZC.

Viewed in the direction of the end 18 of the support plate 3 or in the direction of the patient's feet, the width 31 of the support plate surface 6 of the support plate 3 decreases continuously from its widest point in the front zone ZF to a narrow intermediate piece 30 in the center zone ZC. From there, it widens again continuously up to the end of the support plate 3 in the end zone ZE. Thus, the left cut-out 33 and the right cut-out 32 are formed. The left cut-out 33 and the right cut-out 32 extend in a horizontal direction, preferably they are arranged horizontally, and they are symmetrical to the longitudinal and symmetrical axis 20.

The width 31 of the support plate surface 6 can decrease according to the principles of a plane curve.

The plane curve can be a straight line or a parabola or a circle or an ellipse or a hyperbola.

The plane curve can optionally be comprised of parts of a straight line and/or a parabola and/or a circle and/or an ellipse and/or a hyperbola.

In the intermediate space 14, with the left planar section 39 and the right planar section 40, formed on the upper side 29 of the base plate 2 by the elevated projection of the left cut-out 33 and the right cut-out 32, respectively, a left working space 49 and a right working space 50, respectively, are formed. In the working space 49 and/or 50, the device for immobilizing a breast 22 is arranged. The device for immobilizing a breast 22 is supported, either directly or indirectly, on the base plate 2 and is directly or indirectly connected to it, positively or adhesively.

In the left working space 49 and/or in the right working space 50, in addition to the device for immobilizing a breast 22, a holding device 41 for a medical tool can also be arranged. The holding device 41 for the medical tool is supported directly or indirectly on the base plate 2. The holding device 41 can be positively or adhesively connected to the device for immobilizing a breast 22.

The device for immobilizing a breast 22 can be arranged within the left working space 49 and/or within the right working space 50, so as to be capable of rotating around a vertical axis 42, 43 and locked in place.

In the left working space 49 and/or in the right working space 50, at least one left and/or one right, horizontally oriented MRI-capable receiving surface coil 37, 38 can be arranged.

In the left working space 49 and/or in the right working space 50, inside of, or on or under the base plate 2 a mounting device 11, which is configured to hold at least one MRI-capable receiving surface coil 37, 38, can be arranged.

The mounting device 11 can be displaceable horizontally, crosswise to the longitudinal and symmetrical axis 20.

The mounting device 11 can have one or two devices 12, 13 for holding a device for immobilizing a breast 22, either with or without a holding device 41 for a medical tool.

The device for immobilizing a breast 22, with or without a holding device 41, can be connected directly or indirectly to the base plate 2 via an optionally detachable and lockable non-positive or positive coupling 12, 13.

In the left working space 49 and/or in the right working space 50, two MRI-capable receiving surface coils 44, 45, spaced from one another and parallel to one another, can be arranged, oriented vertically. One or both of the vertically oriented, MRI-capable receiving surface coils 41, 45, spaced from one another, can be secured to the device for immobilizing a breast 22.

However, one or both of these vertically oriented, MRI-capable receiving surface coils 41, 45, which are spaced apart from one another, could also be attached to the inner surface 46 of the end plate (9).

The patient support can have an upper left 47 and/or an upper right MRI-capable receiving surface coil 48, which operate in the left working space 49 and/or the right working space 50, respectively. The upper left 47 and/or the upper right 48 MRI-capable receiving surface coil can be attached directly or indirectly on the support plate 3.

While preferred embodiments of a patient support, in accordance with the present invention, have been set forth fully and completely hereinabove, it will be apparent to one of skill in the art that various changes in, for example, the specific material used to form the patient support, the overall size of the support, and the like could be made without departing from the true spirit and scope of the present invention which is accordingly to be limited only by the appended claims.

What is claimed is:
1. A patient support comprising:
    a unitary support plate including a support plate upper surface and a support plate lower surface, said support plate being symmetrical about a longitudinal axis of symmetry;

a base plate arranged beneath said support plate and spaced from said support plate by an intermediate space, said base plate including a base plate upper surface;

at least one support pillar located in said intermediate space and connecting said base plate upper surface and said support plate lower surface, said at least one support pillar being aligned with said longitudinal axis of symmetry and having a forward end and a rearward end;

at least three successive patient support zones defined by said unitary support plate, said three successive patient support zones including a front zone having a front zone width, a center zone having a center zone width and an end zone having an end zone width, said center zone width bring less than said front zone width and said end zone width, said center zone including a narrow, patient sternum receiving bridge positioned between said front zone and said end zone, said at least one support pillar underlying only said front zone of said support plate and not underlying said patient sternum receiving bridge;

a left cut-out and a right cut-out defining said center zone of said support plate with said cut-outs being spaced on opposite sides of said longitudinal axis of symmetry which extends along said narrow, patient sternum receiving bridge, and being arranged symmetrically with respect to said longitudinal axis of symmetry of said three patient support zones;

a left working space and a right working space formed in said intermediate space below said support plate and above said base plate support surface by a projection of said respective left cut-out and said right cut-out;

a mounting recess in said upper surface of said base plate, said mounting recess extending across said upper surface of said base plate and underlying said left cut-out and said right cut-out;

a patient breast immobilization device positioned in a breast receiving area of said intermediate space, which breast receiving area is defined by said left cut-out and said right cut-out, said patient breast immobilization device being supported by said base plate and extending across said intermediate space below said center zone on both sides of said longitudinal axis of symmetry; and a mounting plate positioned in said mounting recess to connect said patient breast immobilization device to said base plate for rotation of said patient breast immobilization device about a vertical axis and to lock said patient breast immobilization device in place at a specific angle of rotation in at least one of said left and said right working space.

2. The patient support of claim 1 wherein said patient breast immobilization device includes a detachable and lockable coupling engageable with said mounting plate.

3. The patient support of claim 1 further including means supporting said mounting plate for movement with respect to said base plate in said transverse direction.

4. The patient support of claim 1 wherein said patient breast immobilization device is attached to said mounting plate using one of a positive and non-positive coupling.

5. The patient support of claim 1 further including a medical tool holding device arranged in said intermediate space in at least one of said left working zone and said right working zone and supported against said base plate.

6. The patient support of claim 5 wherein said holding device is connected to said patient breast immobilization device.

7. The patient support of claim 1 further including at least one MRI-capable receiving surface coil on said base plate.

8. The patient support of claim 1 further including at least one MRI-capable receiving surface coil mounting device on said base plate.

9. The patient support of claim 1 further including at least one horizontally oriented MRI-capable receiving surface coil on said mounting plate.

10. The patient support of claim 1 further including at least one vertically oriented MRI-capable receiving surface coil on said device and usable for immobilization of a patient's breast.

11. The patient support device of claim 1 further including two vertically oriented and spaced apart MRI-capable receiving surface coils in said intermediate space, arranged parallel to each other and spaced from each other in each said left working space and said right working space.

12. The patient support of claim 11 further including an end plate of said patient support, said end plate having an inner surface, said end plate extending between said support plate and said base plate, said two vertically spaced MRI-capable receiving surface coils being attached to said end plate inner surface.

13. The patient support of claim 1 further including at least one of an upper right MRI-capable receiving surface coil and an upper left MRI-capable receiving surface coil in said intermediate space defined by said at least one of said right and left working spaces on said base plate and attached to said support plate.

14. A patient support comprising:
a unitary support plate including a support plate upper surface and a support plate lower surface said support plate being symmetrical about a longitudinal axis of symmetry;

a base plate arranged beneath said support plate and spaced from said support plate by an intermediate space, said base plate including a base plate upper surface;

at least one support pillar located in said intermediate space and connecting said base plate upper surface and said support plate lower surface said at least our support pillar being aligned with said longitudinal axis of symmetry and having a forward end and a rearward end;

at least three successive patient support zones defined by said unitary plate, said three successive patient support zones including a front zone having a front zone width, a center zone having a center zone width and an end zone having an end zone width, said center zone width being less than said front zone width and said end zone width, said center zone including a narrow patient sternum receiving bridge positioned between said front zone and said end zone, said at least one support pillar underlying only said front zone and not underlying said patient sternum receiving bridge;

a left cut-out and a right cut-out defining said narrow, patient receiving bridge of said center zone and being arranged symmetrically with respect to said longitudinal central axis of said three patient-support zones;

a left working zone and a right working zone formed in said intermediate space below said support plate and above said base plate support surface and defined by a projection of said respective left cut-out and said right cut-out;

a patient breast immobilization device positioned in a breast receiving area of said intermediate space, which breast receiving area is defined by said left cut-out and said right cut-out, said patient breast immobilization device being supported by said base plate and extending across said intermediate space below said center zone on both sides of solid longitudinal axis of symmetry;

a mounting recess in said upper surface of said base plate, said mounting recess extending across said upper surface of said base plate and underlying said left cut-out and said right cut-out;

a mounting plate positioned in said mounting recess to connect said patient breast immobilization device to said base plate and to secure said patient breast immobilization device at a specific angle of rotation; and at least one of an upper left MRI-capable receiving surface coil and an upper right MRI-capable receiving surface coil in each of said at least one of said left working zone and said right working zone in said intermediate space with each of said upper left MRI-capable receiving surface coil and said upper right MRI-capable receiving surface coil being attached to said support plate.

15. The patient support of claim 14 wherein said patient breast immobilization device for is located in said intermediate space in at least one of said left working zone and said right working zone.

16. The patient support of claim 14 wherein said patient breast immobilization device is adapted to be rotatable about a vertical axis and to be locked in place in said at least one of said left working zone and said right working zone.

17. The patient support of claim 14 wherein said patient breast immobilization device is connected to said base plate in one of a positive and an adhesive manner.

18. The patient support of claim 14 wherein said patient breast immobilization device is connected to said base plate using one of a positive and non-positive coupling.

19. The patient support of claim 14 further including means supporting said mounting plate for movement with respect to said base plate in said transverse direction.

20. The patient support of claim 14 further including means on said mounting plate to receive said device for immobilizing a patient's breast.

21. The patient support of claim 14 wherein said patient breast immobilization device is attached to said mounting plate using one of a positive and non-positive coupling.

22. The patient support of claim 14 further including a medical tool holding device arranged in said intermediate space in at least one of said left working zone and said right working zone and supported against said base plate.

23. The patient support of claim 22 wherein said medical tool holding device is connected to said device for immobilization of a patient's breast.

24. The patient support of claim 14 further including at least one MRI-capable receiving surface coil at said base plate.

25. The patient support of claim 14 further including at least one MRI-capable receiving surface coil mounting device at said base plate.

26. The patient support of claim 14 further including at least one horizontally oriented MRI-capable receiving surface coil on said mounting plate.

27. The patient support of claim 14 further including at least one vertically oriented MRI-capable receiving surface coil on said patient breast immobilization device.

28. The patient support of claim 14 further including two vertically oriented and spaced apart MRI-capable receiving surface coils arranged parallel to each other in said left working zone and said right working zone.

29. The patient support of claim 28 further including an end plate of said patient support, said end plate having an inner surface, said end plate extending between said support plate and said base plate, said two vertically spaced MRI-capable receiving surface coils being attached to said end plate inner surface.

30. A patient support comprising:

a unitary support plate including a support plate upper surface and a support plate lower surface, said support plate having a longitudinal axis;

a base plate arranged beneath said support plate and spaced from said support plate by an intermediate space, said base plate including a base plate upper surface;

at least one support pillar located in said intermediate space and connecting said base plate upper surface and said support plate lower surface, said at least one support pillar being aligned with said longitudinal axis and having a forward end and a rearward end;

at least three successive patient support zones defined by said unitary support plate, said three successive patient support zones including a front zone having a front zone width, a center zone having a center zone width and an end zone having an end zone width, said center zone width bring less than said front zone width and said end zone width, said center zone including a narrow, patient sternum receiving bridge positioned between said front zone and said end zone, said at least one support pillar underlying said front zone of said support plate and not underlying said patient sternum receiving bridge;

a left cut-out and a right cut-out defining said center zone of said support plate with said cut-outs being spaced on opposite sides of said longitudinal axis which extends along said narrow, patient sternum receiving bridge, and being arranged symmetrically with respect to said longitudinal axis of said three patient support zones defined by said unitary support plate;

a left working space and a right working space formed in said intermediate space below said support plate and above said base plate support surface by a projection of said respective left cut-out;

a patient breast immobilization device positioned in a breast receiving area of said intermediate space, which breast receiving area is defined by said left cut-out and said right cut-out, said patient breast immobilization device being supported by said base plate and extending across said intermediate space below said center zone on both sides of said longitudinal axis of symmetry; and a mounting plate positioned on said base plate upper surface to connect said patient breast immobilization device to said base plate to allow rotation of said patient breast immobilization device through 360° about a vertical axis relative to a patient breast and to lock said patient breast immobilization device in place at a specific selected angle of rotation with respect to the patient breast in at least one of said left and said right working space.

* * * * *